United States Patent
Skuballa et al.

[11] Patent Number: 5,859,054
[45] Date of Patent: Jan. 12, 1999

[54] LEUKOTRIENE B4 DERIVATIVES, PROCESS FOR THEIR PRODUCTION AND THEIR USE AS PHARMACEUTICAL AGENTS

[75] Inventors: Werner Skuballa; Bernd Buchmann; Josef Heindl; Wolfgang Frohlich; Roland Ekerdt; Claudia Giesen, all of Berlin, Germany

[73] Assignee: Schering Aktiengesellschaft, Berlin, Germany

[21] Appl. No.: 682,724
[22] PCT Filed: Jan. 27, 1994
[86] PCT No.: PCT/EP94/00216
§ 371 Date: Nov. 8, 1996
§ 102(e) Date: Nov. 8, 1996
[87] PCT Pub. No.: WO95/20564
PCT Pub. Date: Aug. 3, 1995

[51] Int. Cl.$^6$ ................................ A61K 31/215
[52] U.S. Cl. .............. 514/529; 514/557; 514/613; 514/729; 554/227; 554/230; 560/106; 560/126; 560/231; 562/508; 564/124; 568/670
[58] Field of Search ................. 560/106, 126, 560/231; 562/508; 564/123; 554/227, 230; 568/670; 514/529, 557, 613, 729

*Primary Examiner*—Michael L. Shippen
*Attorney, Agent, or Firm*—Millen, White, Zelano, & Branigan, P.C.

[57] ABSTRACT

Pharmacologically active leukotriene-$B_4$ derivatives of general formula I,

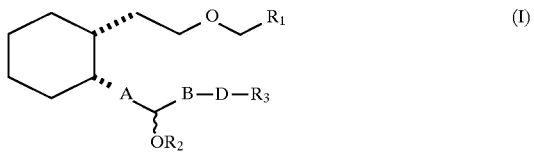

are described,
in which $R_1$ represents $CH_2OH$, $CH_3$, $CF_3$, $COOR_4$, $CONR_5R_6$, or $R_2$ represents H or an organic acid radical with 1–15 C atoms, $R_3$ symbolizes H; $C_1$–$C_{14}$ alkyl, $C_3$–$C_{10}$ cycloalkyl optionally substituted singly or multiply; $C_6$–$C_{10}$ aryl radicals, independently of one another, optionally substituted singly or multiply by halogen, phenyl, $C_1$–$C_4$ alkyl, $C_1$–$C_4$ alkoxy, fluoromethyl, chloromethyl, trifluoromethyl, carbonyl, carboxyl or hydroxy; or a 5- to 6-membered aromatic heterocyclic ring with at least 1 heteroatom, $R_4$ means hydrogen, $C_1$–$C_{10}$ alkyl, $C_3$–$C_{10}$ cycloalkyl; $C_6$–$C_{10}$ aryl radicals optionally substituted by 1–3 halogen, phenyl, $C_1$–$C_4$ alkyl, $C_1$–$C_4$ alkoxy, fluoromethyl, chloromethyl, trifluoromethyl, carboxyl or hydroxy; $CH_2$—CO—($C_6$–$C_{10}$) aryl or a 5- to 6-membered ring with at least 1 heteroatom, A symbolizes a trans, trans—CH=CH—CH=CH, a —$CH_2CH_2$—CH=CH— or a tetramethylene group, B symbolizes a $C_1$–$C_{10}$ straight-chain or branched-chain alkylene group, which optionally can be substituted by fluorine or the group

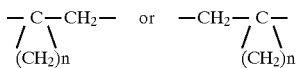

D means a direct bond, oxygen, sulfur, —C≡C—, —CH=$CR_7$, or together with B can also mean a direct bond, $R_5$ and $R_6$ are the same or different, and represent H or $C_1$–$C_4$ alkyl or $R_6$ represents H and $R_5$ represents $C_1$–$C_{15}$ alkanoyl or $R_8SO_2$, and are optionally substituted with OH, $R_7$ means H, $C_1$–$C_5$ alkyl, chlorine, bromine, $R_8$ has the same meaning as $R_3$, n is 2–5, and, if $R_4$ means hydrogen, their salts with physiologically compatible bases and their cyclodextrin clathrates.

21 Claims, No Drawings

LEUKOTRIENE B4 DERIVATIVES, PROCESS FOR THEIR PRODUCTION AND THEIR USE AS PHARMACEUTICAL AGENTS

The invention relates to new leukotriene-$B_4$ derivatives, process for their production and their use as pharmaceutical agents. The new compounds are optically active structural analogues of previously known leukotriene-$B_4$ antagonists, which contain a six-membered ring as a basic structural element (DE-A 39 17 597, DE-A 42 27 790.6). Leukotriene $B_4$ ($LTB_4$) was discovered by B. Samuelsson et al. as a metabolite of the arachidonic acid. In the biosynthesis, leukotriene $A_4$ is formed by the enzyme 5-lipoxygenase first as a central intermediate product, which then is converted by a specific hydrolase to the $LTB_4$.

B. Samuelsson, Sciences 237, 1171 (1987). d) C. W. Parker, Drug Development Research 10, 277 (1987). It follows from the above that $LTB_4$ is an important inflammation mediator for inflammatory diseases, in which leukocytes invade the affected tissue.

The effects of $LTB_4$ are triggered on the cellular plane by the bond of $LTB_4$ on a specific receptor.

It is known concerning $LTB_4$ that it causes the adhesion of leukocytes on the blood vessel wall. $LTB_4$ is chemotactically effective, i.e., it triggers a directed migration of leukocytes in the direction of a gradient of increasing concentration. Furthermore, it indirectly changes the vascular permeability based on its chemotactic activity, and a synergism with prostaglandin $E_2$ is observed. $LTB_4$ obviously plays a decisive role in inflammatory, allergic and immunological processes.

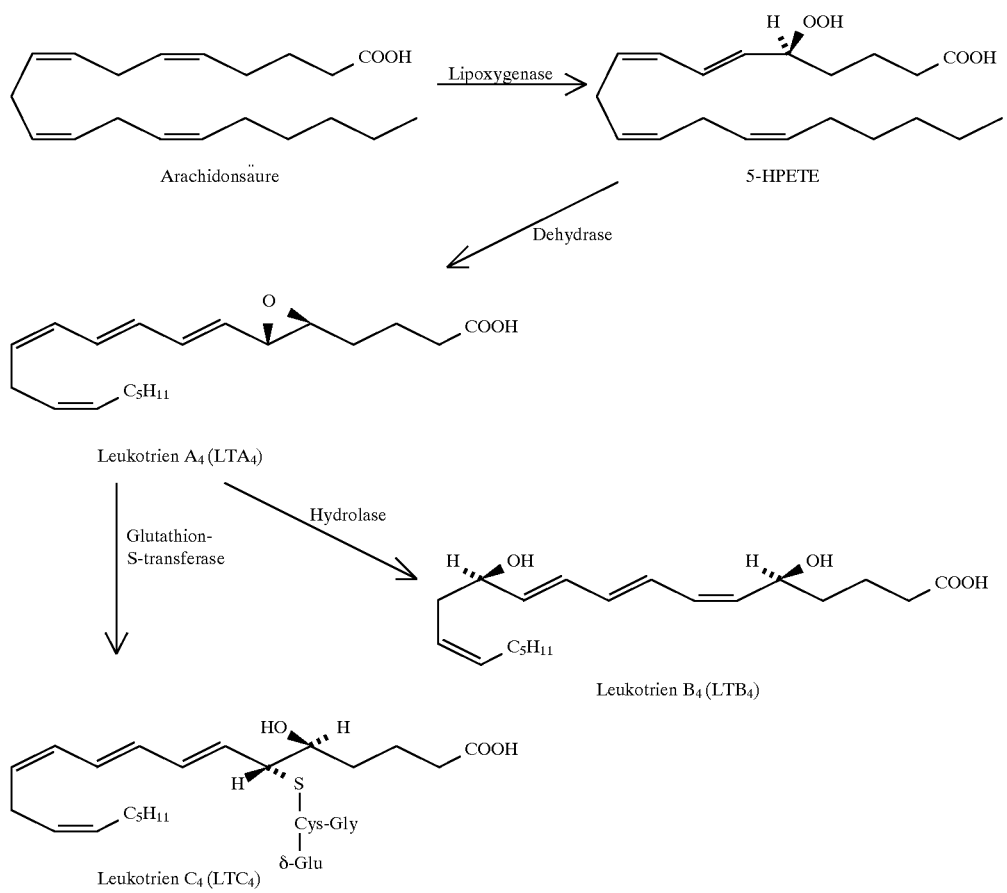

KEY:
Arachidonsäure = arachidonic acid
Leukotrien $A_4$ ($LTA_4$) = leukotriene $A_4$ ($LTA_4$)
Glutathion – S-transferase = glutathione – S-transferase
Leukotrien $B_4$ ($LTB_4$) = leukotriene $B_4$ ($LTB_4$)
Leukotrien $C_4$ ($LTC_4$) = leukotriene $C_4$ ($LTC_4$)

The nomenclature of the leukotrienes can be gathered from the following works:
a) B. Samuelsson et al., Prostaglandins 19, 645 (1980); 17, 785 (1979).
b) C. N. Serhan et al., Prostaglandins 34, 201 (1987).

The physiological and especially the pathophysiological importance of leukotriene $B_4$ is summarized in several more recent works: a) The Leukotrienes, Chemistry and Biology eds. L. W. Chakrin, D. M. Bailey, Academic Press 1984. b) J. W. Gillard et al., Drugs of the Future 12, 453 (1987). c)

Leukotrienes and especially $LTB_4$ are involved in skin diseases, which are accompanied by inflammatory processes (increased vascular permeability and formation of edemas, cell infiltration), increased proliferation of skin cells and itching, such as, for example, in eczemas, erythemas, psoriasis, pruritus and acne. Pathologically increased leukotriene concentrations are involved either causally in the development of many dermatitides or there is a connection between the persistence of the dermatitides and the leukotrienes. Clearly increased leukotriene concentrations were measured, for example, in the skin of patients with psoriasis or atopic dermatitis.

Leukotrienes and especially LTB$_4$ are also involved in the diseases of internal organs, for which an acute or chronic inflammatory component was described, e.g.: joint diseases (arthritis); diseases of the respiratory tract (asthma, rhinitis and allergies); inflammatory intestinal diseases (colitis); as well as reperfusion damages (to the heart, intestinal or renal tissues), which result by the temporary pathological obstruction of blood vessels.

Further, leukotrienes and especially LTB$_4$ are involved in the disease of multiple sclerosis and in the clinical picture of shock (triggered by infections, burns or in complications in kidney dialysis or other separately discussed perfusion techniques).

Leukotrienes and especially LTB$_4$ further have an effect on the formation of white blood cells in the bone marrow, on the growth of unstriped muscle cells, of keratinocytes and of B-lymphocytes. LTB$_4$ is therefore involved in diseases with inflammatory processes and in diseases with pathologically increased formation and growth of cells.

For example, leukemia or arteriosclerosis represent diseases with this clinical picture.

By the antagonizing of the effects, especially by LTB$_4$, the active ingredients and their forms of administration of this invention are specific medicines for diseases of humans and animals, in which especially leukotrienes play a pathological role.

Besides the therapeutic possibilities, which can be derived from an antagonizing of LTB$_4$ action with LTB$_4$ analogues, the usefulness and potential use of leukotriene-B$_4$ agonists for the treatment of fungus diseases of the skin were also able to be shown (H. Katayama, Prostaglandins 34, 797 (1988)).

The invention relates to leukotriene-B$_4$ derivatives of general formula I

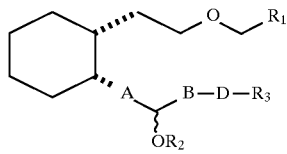

in which

R$_1$ represents CH$_2$OH, CH$_3$, CF$_3$, COOR$_4$, CONR$_5$R$_6$, or

R$_2$ represents H or an organic acid radical with 1–15 C atoms,

R$_3$ symbolizes H; C$_1$–C$_{14}$ alkyl, C$_3$–C$_{10}$ cycloalkyl optionally substituted singly or multiply; C$_6$–C$_{10}$ aryl radicals, independently of one another, optionally substituted singly or multiply by halogen, phenyl, C$_1$–C$_4$ alkyl, C$_1$–C$_4$ alkoxyl, fluoromethyl, chloromethyl, trifluoromethyl, carbonyl, carboxyl or hydroxy; or a 5- to 6-membered aromatic heterocyclic ring with at least 1 heteroatom, R$_4$ means hydrogen, C$_1$–C$_{10}$ alkyl, C$_3$–C$_{10}$ cycloalkyl; C$_6$–C$_{10}$ aryl radicals optionally substituted by 1–3 halogen, phenyl, C$_1$–C$_4$ alkyl, C$_1$–C$_4$ alkoxy, fluoromethyl, chloromethyl, trifluoromethyl, carboxyl or hydroxy; CH$_2$—CO—(C$_6$–C$_{10}$) aryl or a 5- to 6-membered ring with at least 1 heteroatom, A symbolizes a trans, trans—CH═CH—CH═CH, a —CH$_2$CH$_2$—CH═CH— or a tetramethylene group, B symbolizes a C$_1$–C$_{10}$ straight-chain or branched-chain alkylene group, which optionally can be substituted by fluorine or the group

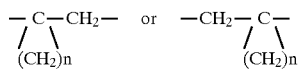

D means a direct bond, oxygen, sulfur, —C≡C—, —CH═CR$_7$, or together with B can also mean a direct bond, R$_5$ and R$_6$ are the same or different, and represent H or C$_1$–C$_4$ alkyl or R$_6$ represents H and R$_5$ represents C$_1$–C$_{15}$ alkanoyl or R$_8$SO$_2$, and optionally are substituted with OH, R$_7$ means H, C$_1$–C$_5$ alkyl, chlorine, bromine, R$_8$ has the same meaning as R$_3$, n is 2–5, and, if R$_4$ means hydrogen, their salts with physiologically compatible bases and their cyclodextrin clathrates.

The group OR$_2$ can be in α- or β-position. Formula I comprises both racemates and the possible pure diastereomers and enantiomers.

As alkyl groups R$_4$, straight-chain or branched-chain alkyl groups with 1–10 C atoms are considered, such as, for example, methyl, ethyl, propyl, butyl, isobutyl, tert-butyl, pentyl, neopentyl, hexyl, heptyl, decyl.

Alkyl groups R$_4$ can optionally be substituted singly to multiply by halogen atoms, alkoxy groups, optionally substituted aryl or aroyl groups with 6–10 C atoms (relative to possible substituents, see under aryl R$_4$), dialkylamino and trialkylammonium with 1–4 C atoms in the alkyl portion, whereby the single substitution is to be preferred. As substituents, for example, fluorine, chlorine or bromine, phenyl, dimethylamino, diethylamino, methoxy, ethoxy can be mentioned. As preferred alkyl groups R$_4$, those with 1–4 C atoms can be mentioned.

Cycloalkyl group R$_4$ can contain 3–10, preferably 5 and 6 carbon atoms in the ring. The rings can be substituted by alkyl groups with 1–4 carbon atoms. For example, cyclopentyl, cyclohexyl, methylcyclohexyl can be mentioned.

As aryl groups R$_4$, both substituted and unsubstituted aryl groups with 6–10 C atoms are considered, such as, for example, phenyl, 1-naphthyl and 2-naphthyl, which can be substituted in each case by 1–3 halogen atoms (F, Cl, Br), a phenyl group, 1–3 alkyl groups with, in each case, 1–4 C atoms, a chloromethyl, a fluoromethyl, trifluoromethyl, carboxyl, hydroxy or alkoxy group with 1–4 C atoms. Preferred substituents in 3- and 4-position on the phenyl ring are, for example, fluorine, chlorine, alkoxy or trifluoromethyl, in 4-position, however, hydroxy.

As heterocyclic groups R$_4$, 5- and 6-membered aromatic heterocycles are suitable, which contain at least 1 heteroatom, preferably nitrogen, oxygen or sulfur. For example, 2-furyl, 2-thienyl, 2-pyridyl, 3-pyridyl, 4-pyridyl, oxazolyl, thiazolyl, pyrimidinyl, pyridazinyl, 3-furyl, 3-thienyl, 2-tetrazolyl, i.a., can be mentioned.

As acid radical R$_5$, such physiologically compatible acids are suitable. Preferred acids are organic carboxylic acids and sulfonic acids with 1–15 carbon atoms, which belong to the aliphatic, cycloaliphatic, aromatic, aromatic-aliphatic and heterocyclic series. These acids can be saturated, unsaturated and/or polybasic and/or substituted in the usual way. As examples of the substituents, C$_{1-4}$ alkyl, hydroxy, C$_{1-4}$ alkoxy, oxo or amino groups or halogen atoms (F, Cl, Br) can be mentioned. For example, the following carboxylic acids can be mentioned: formic acid, acetic acid, propionic acid, butyric acid, isobutyric acid, valeric acid, isovaleric acid, caproic acid, oenanthic acid, caprylic acid, pelargonic acid, capric acid, undecylic acid, lauric acid, tridecylic acid, myristic acid, pentadecylic acid, trimethylacetic acid, diethylacetic acid, tert-butylacetic acid, cyclopropylacetic acid, cyclopentylacetic acid, cyclohexylacetic acid, cyclopropanecarboxylic acid, cyclohexanecarboxylic acid, phenylacetic acid, phenoxyacetic acid, methoxyacetic acid, ethoxyacetic acid, mono-, di- and trichloroacetic acid, aminoacetic acid, diethylaminoacetic acid, piperidinoacetic acid, morpholinoacetic acid, lactic acid, succinic acid, adipic acid, benzoic acid; benzoic acids substituted with halogen (F, Cl, Br) or trifluoromethyl, hydroxy, $C_{1-4}$ alkoxy or carboxy groups; nicotinic acid, isonicotinic acid, furan-2-carboxylic acid, cyclopentylpropionic acid. As preferred arylsulfonyl radicals and alkanesulfonyl radicals $R_8SO_2$, those are to be considered that are derived from a sulfonic acid with up to 10 carbon atoms. As sulfonic acids, for example, methanesulfonic acid, ethanesulfonic acid, isopropanesulfonic acid, β-chloroethanesulfonic acid, butanesulfonic acid, cyclopentanesulfonic acid, cyclohexanesulfonic acid, benzenesulfonic acid, p-toluenesulfonic acid, p-chlorobenzenesulfonic acid, N,N-dimethylaminosulfonic acid, N,N-diethylaminosulfonic acid, N,N-bis-(β-chloroethyl)-aminosulfonic acid, N,N-diisobutylaminosulfonic acid, N,N-dibutylaminosulfonic acid, pyrrolidino, piperidino, piperazino, M-methylpiperazino and morpholinosulfonic acid are suitable.

As alkyl groups $R_3$, straight-chain and branched-chain, saturated and unsaturated alkyl radicals, preferably saturated, with 1–14, especially 1–10 C atoms, are suitable, which optionally can be substituted by optionally substituted phenyl (for substitution, see under aryl $R_5$). For example, methyl, ethyl, propyl, butyl, isobutyl, tert-butyl, pentyl, hexyl, heptyl, octyl, butenyl, isobutenyl, propenyl, pentenyl, benzyl, m- and p-chlorobenzyl groups can be mentioned. If alkyl groups $R_3$ are halogen-substituted, fluorine, chlorine and bromine are suitable as halogens.

As examples of halogen-substituted alkyl groups $R_3$, alkyls with terminal trifluoromethylene groups are considered.

Cycloalkyl group $R_3$ can contain 3–10, preferably 3–6 carbon atoms in the ring. The rings can be substituted by alkyl groups with 1–4 carbon atoms optionally by halogens. For example, cyclopropyl, cyclobutyl, cyclopentyl, cyclohexyl, methyl-cyclohexyl, fluorocyclohexyl can be mentioned.

As substituted or unsubstituted aryl groups $R_3$, for example, phenyl, 1-naphthyl and 2-naphthyl, which can be substituted in each case by 1–3 halogen atoms (F, Cl, Br), a phenyl group, 1–3 alkyl groups with 1–4 C atoms in each case, a chloromethyl, fluoromethyl, trifluoromethyl, carboxyl, $C_1$–$C_4$ alkoxy or hydroxy group, are considered. Preferred is the substitution in 3- and 4-position on the phenyl ring by, for example, fluorine, chlorine, alkoxy or trifluoromethyl or in 4-position by hydroxy.

As heterocyclic aromatic groups $R_3$, 5- and 6-membered heterocycles that contain at least 1 heteroatom, preferably nitrogen, oxygen or sulfur, are suitable. For example, 2-furyl, 2-thienyl, 2-pyridyl, 3-pyridyl, 4-pyridyl, oxazolyl, thiazolyl, pyrimidinyl, pyridazinyl, pyrazinyl, 3-furyl, 3-thienyl, i.a., can be mentioned.

As alkylene group B, straight-chain or branched, saturated or unsaturated alkylene radicals, preferably saturated with 1–10, especially with 1–5 C atoms, are suitable, which optionally can be substituted by fluorine atoms. For example, methylene, fluoromethylene, difluoromethylene, ethylene, 1,2-propylene, ethylethylene, trimethylene, tetramethylene, pentamethylene, 1,2-difluoroethylene, 1-fluoroethylene, 1-methyltetramethylene, 1-methyl-trimethylene, 1-methylene-ethylene, 1-methylene-tetramethylene can be mentioned.

Alkylene group B can further represent the group

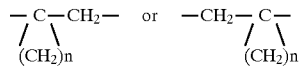

whereby n=2–5, preferably 3–5.

As acid radicals $R_2$, those of physiologically compatible acid radicals are suitable. Preferred acids are organic carboxylic acids and sulfonic acids with 1–15 carbon atoms, which belong to the aliphatic, cycloaliphatic, aromatic, aromatic-aliphatic or heterocyclic series. These acids can be substituted saturated, unsaturated and/or polybasic and/or in the usual way. As examples of the substituents, $C_{1-4}$ alkyl, hydroxy, $C_{1-4}$ alkoxy, oxo or amino groups or halogen atoms (F, Cl, Br) can be mentioned. For example, the following carboxylic acids can be mentioned: formic acid, acetic acid, propionic acid, butyric acid, isobutyric acid, valeric acid, isovaleric acid, caproic acid, oenanthic acid, caprylic acid, pelargonic acid, capric acid, undecylic acid, lauric acid, tridecylic acid, myristic acid, pentadecylic acid, trimethylacetic acid, diethylacetic acid, tert-butylacetic acid, cyclopentylacetic acid, cyclohexylacetic acid, cyclohexanecarboxylic acid, phenylacetic acid, phenoxyacetic acid, methoxyacetic acid, ethoxyacetic acid, mono-, di- and trichloroacetic acid, aminoacetic acid, diethylaminoacetic acid, piperidinoacetic acid, morpholinoacetic acid, lactic acid, succinic acid, adipic acid, benzoic acid; benzoic acids substituted with halogen (F, Cl, Br) or trifluoromethyl, hydroxy, $C_{1-4}$ alkoxy or carboxy groups; nicotinic acid, isonicotinic acid, furan-2-carboxylic acid, cyclopentylpropionic acid. As preferred acid radicals $R_2$ and $R_3$, those acyl radicals with up to 10 carbon atoms are considered.

Alkyl radicals $R_5$ and $R_6$, which optionally contain hydroxy groups, are straight-chain or branched alkyl radicals, especially straight-chain, such as, for example, methyl, ethyl, propyl, butyl, pentyl, hexyl, especially preferably methyl.

$R_7$ as $C_{1-5}$ alkyl means straight-chain or branched-chain alkyl radicals as were already mentioned for $R_3$ or $R_4$. Preferred alkyl radicals $R_7$ are methyl, ethyl, propyl and isopropyl.

Inorganic and organic bases are suitable for salt formation, as they are known to one skilled in the art for forming physiologically compatible salts. For example, alkali hydroxides, such as sodium hydroxide and potassium hydroxide, alkaline-earth hydroxides, such as calcium hydroxide, ammonia, amines, such as ethanolamine, diethanolamine, triethanolamine, N-methylglucamine, morpholine, tris-(hydroxymethyl)-methylamine, etc., can be mentioned.

To attain the cyclodextrin clathrates, the compounds of formula I are reacted with α-, β- or γ-cyclodextrin. Preferred are β-cyclodextrin derivatives.

Preferred compounds of this invention are compounds of general formula I, whereby the radicals have the following meaning:

$R_1$ is $CH_2OH$, $CONR_5R_6$, $COOR_4$ with $R_4$ meaning a hydrogen atom, an alkyl radical with 1–10 C atoms, a cycloalkyl radical with 5–6 C atoms, a phenyl radical optionally substituted by 1–2 chlorine, bromine, phenyl, $C_{1-4}$ alkyl, $C_{1-4}$ alkoxy, chloromethyl, fluoromethyl, trifluoromethyl, carboxy or hydroxy, A is a trans—CH=CH—CH=CH or tetramethylene group;

B is a straight-chain or branched-chain, saturated or unsaturated alkylene group with up to 10 C atoms, which optionally can be substituted by fluorine, or the group

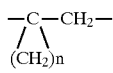

with n=2–5;

D is a direct bond, oxygen, sulfur, a —C≡C group or a —CH=CR$_7$ group with R$_7$ as hydrogen, C$_{1-5}$ alkyl, chlorine or bromine;

B and D are together a direct bond;

R$_2$ means hydrogen or an organic acid radical with 1–15 C atoms;

R$_5$ and R$_6$ have the above-indicated meanings;

R$_3$ is a hydrogen atom, C$_{1-10}$ alkyl, cycloalkyl with 5–6 C atoms, a phenyl radical optionally substituted by 1–2 chlorine, bromine, phenyl, C$_{1-4}$ alkyl, C$_{1-4}$ alkoxy, chloromethyl, fluoromethyl, trifluoromethyl, carboxy or hydroxy, and if R$_4$ means a hydrogen, their salts with physiologically compatible bases and cyclodextrin clathrates.

Especially preferred compounds of this invention are compounds of general formula I, whereby the radicals have the following meaning:

R$_1$ is CH$_2$OH, CONR$_5$R$_6$, COOR$_4$ with R$_4$ meaning a hydrogen atom, an alkyl radical with 1–4 C atoms, R$_2$ means hydrogen or an organic acid radical with 1–6 C atoms, R$_3$ is a hydrogen atom or C$_{1-10}$ alkyl;

R$_5$ and R$_6$ have the above-indicated meanings;

A is a trans, trans—CH=CH—CH=CH or tetramethylene group;

B is a straight-chain or branched-chain alkylene group with up to 5 C atoms;

D is a direct bond or a —C≡C group or a —CH=CR$_7$ group with R$_7$ as hydrogen or C$_{1-5}$ alkyl;

B and D are together a direct bond; and if R$_4$ means a hydrogen atom, their salts with physiologically compatible bases and their cyclodextrin clathrates.

In addition, the invention relates to a process for the production of the compounds of general formula I according to the invention, which is characterized in that an alcohol of formula II,

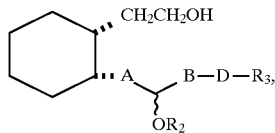 (II)

in which A, B, D, R$_2$ and R$_3$ have the above-indicated meaning, optionally under protection of free hydroxy groups in R$_2$, is reacted with an alkyl halide or haloacetic acid derivative of general formula III,

 (III)

in which X represents chlorine, bromine or iodine, and R$_1$ represents —CH$_3$, CF$_3$, COOR$_4$, CONR$_5$R$_6$ or —CH$_2$OR$_9$, in which R$_9$ means a readily cleavable ether radical, is etherified in the presence of a base and optionally then separated in any sequence of isomers, protected hydroxy groups are released and/or a free hydroxy group is esterified and/or the 1-hydroxy group is oxidized to carboxylic acid and/or double bonds are hydrogenated and/or an esterified carboxyl group is saponified and/or reduced or a carboxyl group is esterified and/or a free carboxyl group is converted to an amide or a carboxyl group is converted to a salt with a physiologically compatible base.

As ether radicals R$_9$ in the compound of formula II, the radicals that are familiar to one skilled in the art are considered. Preferred are readily cleavable ether radicals, such as, for example, dimethyl-tert-butylsilyl, trimethylsilyl, tribenzylsilyl, diphenyl-tert-butylsilyl, tetrahydropyranyl, tetrahydrofuranyl and α-ethoxyethyl, to name only a few.

The reaction of the compound of general formula II with an alkyl halide or a haloacetic acid derivative of general formula III is performed at temperatures of 0° C. to 100° C., preferably at 10° C. to 80° C. in an aprotic solvent or solvent mixture, for example, dimethyl sulfoxide, dimethylformamide, tetrahydrofuran, etc. As bases, the bases known to one skilled in the art for etherification are suitable, for example, sodium hydride, potassium-tert-butylate, butyllithium, etc.

The above-mentioned etherification can also be performed preferably under phase transfer conditions with 20–50% aqueous sodium hydroxide or potassium hydroxide solution without an additional solvent or in an aprotic solvent, such as, for example, toluene, in the presence of a phase transfer catalyst, such as, for example, tetrabutylammonium hydrogen sulfate at temperatures between 0° C. and 90° C., preferably between 20° C. and 60° C.

The reduction to the compounds of formula I with R$_1$ meaning a CH$_2$OH group is performed with a reducing agent that is suitable for the reduction of esters or carboxylic acids, such as, for example, lithium aluminum hydride, diisobutyl aluminum hydride, etc. As a solvent, diethyl ether, tetrahydrofuran, dimethoxyethane, toluene, etc., are suitable. The reduction is performed at temperatures of –30° C. up to boiling temperature of the solvent used, preferably 0° C. to 30° C.

The esterification of the alcohols of formula I (R$_2$=H) is carried out in a way known in the art. For example, the esterification is carried out in that an acid derivative, preferably an acid halide or acid anhydride, is reacted with an alcohol of formula I in the presence of a base such as, for example, NaH, pyridine, triethylamine, tributylamine or 4-dimethylaminopyridine. The reaction can be performed without a solvent or in an inert solvent, preferably acetone, acetonitrile, dimethylacetamide, dimethyl sulfoxide at temperatures above or below room temperature, for example, between –80° C. to 100° C., preferably at room temperature.

The oxidation of the 1-hydroxy group is performed according to methods that are known to one skilled in the art. As oxidizing agents, for example, there can be used: pyridinium dichromate (Tetrahedron Letters, 1979, 399), Jones reagent (J. Chem. Soc. 1953, 2555) or platinum/oxygen (Adv. in Carbohydrate Chem. 17, 169 (1962) or Collins oxidation (Tetrahedron Letters 1968, 3363 and subsequent Jones Oxidation. The oxidation with pyridinium dichromate is performed at temperatures of 0° C. to 100° C., preferably at 20° C. to 40° C. in a solvent that is inert with respect to the oxidizing agent, for example, dimethylformamide.

The oxidation with Jones reagent is carried out at temperatures of –40° C. to +40° C., preferably 0° C. to 30° C., in acetone as a solvent.

The oxidation with platinum/oxygen is performed at temperatures of 0° C. to 60° C., preferably 20° C. to 40° C., in a solvent that is inert with respect to the oxidizing agent, such as, e.g., ethyl acetate.

The saponification of the esters of formula I is performed according to the methods known to one skilled in the art, such as, for example, with basic catalysts. The compounds of formula I can be separated by the conventional separating methods into optical isomers (Asymmetric Synthesis, Vol. 1–5, Ed. J. D. Morrison, Academic Press, Inc., Orlando etc., 1985; Chiral Separations by HPLC, Ed. A. M. Krstulovic; John Wiley & Sons; New York etc. 1989).

The release of the functionally modified hydroxy groups is carried out according to known methods. For example, the cleavage of hydroxy protective groups, such as, for example, the tetrahydropyranyl radical, is performed in an aqueous solution of an organic acid, such as, e.g., oxalic acid, acetic acid, propionic acid, i.a., or in an aqueous solution of an inorganic acid, such as, e.g., hydrochloric acid. To improve the solubility, a water-miscible inert organic solvent is suitably added. Suitable organic solvents are, e.g., alcohols, such as methol and ethanol, and ethers, such as dimethoxyethane, dioxane and tetrahydrofuran. Tetrahydrofuran is preferably used. The cleavage is performed preferably at temperatures between 20° C. and 80° C. The cleavage of the silyl ether protective groups is carried out, for example, with tetrabutylammonium fluoride or with potassium fluoride in the presence of a crown ether (such as, for example, dibenzo[18]-crown-6). As a solvent, for example, tetrahydrofuran, diethyl ether, dioxane, dichloromethane, etc., are suitable. The cleavage is performed preferably at temperatures between 0° C. and 80° C.

The saponification of the acyl groups is carried out, for example, with alkali or alkaline-earth carbonates or -hydroxides in an alcohol or in the aqueous solution of an alcohol. As an alcohol, lower aliphatic alcohols, such as, e.g., methanol, ethanol, butanol, etc., preferably methanol, are considered. As alkali carbonates and -hydroxides, potassium and sodium salts can be mentioned. Preferred are potassium salts.

As alkaline-earth carbonates and -hydroxides, for example, calcium carbonate, calcium hydroxide and barium carbonate are suitable. The reaction is carried out at −10° C. to +70° C., preferably at +25° C.

The introduction of ester group —$COOR_4$ for $R_1$, in which $R_4$ represents an alkyl group with 1–10 C atoms, is carried out according to the methods known to one skilled in the art. The 1-carboxy compounds are reacted, for example, with diazohydrocarbons in a way known in the art. The esterification with diazohydrocarbons is carried out, e.g., in that a solution of the diazohydrocarbon in an inert solvent, preferably in diethyl ether, is mixed with the 1-carboxy compound in the same solvent or in another inert solvent, such as, e.g., methylene chloride. After the reaction is completed in 1 to 30 minutes, the solvent is removed, and the ester is purified in the usual way. Diazoalkanes are either known or can be produced according to known methods [Org. Reactions Vol. 8, pages 389–394 (1954)].

The introduction of ester group —$COOR_4$ for $R_1$, in which $R_4$ represents a substituted or unsubstituted aryl group, is carried out according to the methods known to one skilled in the art. For example, the 1-carboxy compounds are reacted in an inert solvent with the corresponding arylhydroxy compounds with dicyclohexylcarbodiimide in the presence of a suitable base, for example, pyridine, dimethylaminopyridine, triethylamine. As a solvent, methylene chloride, ethylene chloride, chloroform, ethyl acetate, tetrahydrofuran, preferably chloroform, are suitable. The reaction is performed at temperatures between −30° C. and +50° C., preferably at 10° C.

If C═C double bonds that are contained in the primary product are to be reduced, the hydrogenation is carried out according to methods known in the art.

The hydrogenation of the $\Delta^{8,10}$-diene system is performed in a way known in the art at low temperatures, preferably at about −20° C. to +30° C. in a hydrogen atmosphere in the presence of a noble metal catalyst. As a catalyst, for example, 10% palladium on carbon is suitable.

The leukotriene-$B_4$ derivatives of formula I with $R_4$ meaning a hydrogen can be converted to a salt with suitable amounts of the corresponding inorganic bases with neutralization. For example, in dissolving the corresponding acids in water, which contains the stoichiometric amount of the base, the solid inorganic salt is obtained after water is evaporated or after a water-miscible solvent, e.g., alcohol or acetone, is added.

For the production of an amine salt, $LTB_4$ acid is dissolved in, e.g., a suitable solvent, for example, ethanol, acetone, diethyl ether, acetonitrile or benzene, and at least the stoichiometric amount of the amine is added to the solution. In this way, the salt usually accumulates in solid form or is isolated after the solvent is evaporated in the usual way.

The introduction of amide group —$CONHR_5$ with $R_5$ meaning alkanoyl is carried out according to the methods known to one skilled in the art. The carboxylic acids of formula I ($R_4$=H) are first converted to the mixed anhydride in the presence of a tertiary amine, such as, for example, triethylamine, with chloroformic acid butyl ester. The reaction of the mixed anhydride with the alkali salt of the corresponding amide or with ammonia ($R_5$=H) is carried out in an inert solvent or solvent mixture, such as, for example, tetrahydrofuran, dimethoxyethane, dimethylformamide, hexamethylphosphoric acid triamide, at temperatures between −30° C. and +60° C., preferably at 0° C. to 30° C. Another type of production of the amides involves the amidolysis of 1-ester ($R_1$=$COOR_4$) with the corresponding amine.

Another possibility for the introduction of amide group —$CONHR_5$ involves the reaction of a 1-carboxylic acid of formula I ($R_4$=H), in which free hydroxy groups are optionally intermediately protected, with compounds of formula IV, $$O=C=N-R_5 \qquad \text{(IV)}$$

in which $R_5$ has the above-indicated meaning.

The reaction of the compound of formula I ($R_4$=H) with an isocyanate of formula IV is carried out optionally with the addition of a tertiary amine, such as, e.g., triethylamine or pyridine. The reaction can be performed without a solvent or in an inert solvent, preferably acetonitrile, tetrahydrofuran, acetone, dimethylacetamide, methylene chloride, diethyl ether, toluene, at temperatures between −80° C. to 100° C., preferably at 0° C. to 30° C.

For the production of the other amides, for example, the desired acid anhydride can be reacted with ammonia or the corresponding amines.

If the starting product contains OH groups in the leukotriene-$B_4$ radical, these OH groups are also brought to reaction. If end products that contain free hydroxyl groups are ultimately desired, a start is suitably made from starting products in which the latter are intermediately protected by preferably readily cleavable ether or acyl radicals.

The separation of the diastereomers is carried out according to methods known to one skilled in the art, for example by column chromatography.

The compounds of formula II that are used as starting material can be produced, for example, by cis-1,2-diacetoxymethyl-cyclohex-4-ene or cis-1,2-diacetoxymethyl-cyclohexane being enantioselectively hydrolyzed with a lipase in a way known in the art (J. B. Jones et al., J. Chem. Soc. Chem. Commun. 1985, 1563; M. Schneider et al., Tetrahedron Lett. 26, 2073 (1985); H. J. Gais et al., Tetrahedron Lett. 28, 3471 (1987)). The optically active monoacetate that is produced in this way is then converted to the tert-butyldimethylsilyl ether, optionally hydrogenated and then converted with diisobutyl aluminum hydride to the monosilyl ether of formula V

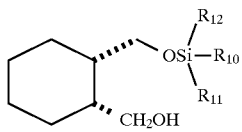
(V)

in which $R_{10}$, $R_{11}$ and $R_{12}$ are the same or different and mean $C_1$–$C_4$ alkyl or phenyl.

By the oxidation, e.g., with Collins reagent or by the Swern process (Tetrahedron Letters 34, 1651 (1978)), the aldehyde of formula VI is obtained

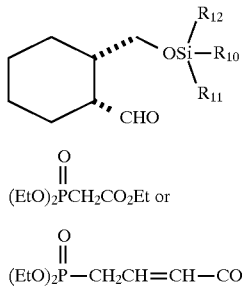
(VI)

(EtO)$_2$PCH$_2$CO$_2$Et or (VII)

(EtO)$_2$P—CH$_2$CH=CH—COOEt (VIII)

which is converted in a Wittig-Horner olefination with the phosphonate of formula VII and a base and optionally subsequent hydrogenation as well as subsequent reduction of the ester group, oxidation of the primary alcohol, repeated Wittig-Horner olefination with the phosphonate of formula VII and optionally subsequent hydrogenation to the ester of formula IX or a Wittig-Horner reaction of the aldehyde of formula VI with a phosphonate of formula VIII, whereby A

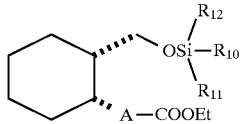
(IX)

has the above-indicated meaning. As bases, for example, potassium tert-butylate, diazabicyclononane, diazabicycloundecane or sodium hydride are suitable. Reduction of the ester group, for example with diisobutyl aluminum hydride, and subsequent oxidation of the primary alcohol obtained, e.g., with manganese dioxide or Collins reagent, results in an aldehyde of formula X

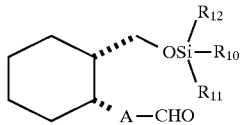
(X)

The organometallic reaction of the aldehyde of formula X with a Grignard reagent of formula XI, in which B, D

X—Mg—B—D—R$_3$ (XI)

and $R_4$ have the above-indicated meanings and X means chlorine, bromine or iodine, results, under protection of the hydroxy groups (for example by acylation) and optionally diastereomer separation, in the compounds of formula XII

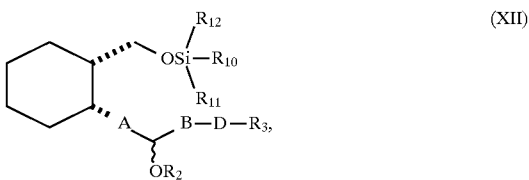
(XII)

The production of the compound of formula XI that is required for the organometallic reaction is carried out by reaction of the corresponding terminal halide with magnesium. By reaction of silyl ether XII with tetrabutylammonium fluoride and optionally diastereomer separation, the alcohol of formula XIII is obtained.

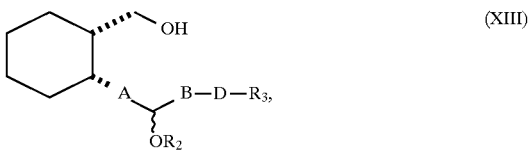
(XIII)

The compounds of formula XII, in which B means a CH$_2$ group and D means a —C≡C group or a CH=CR$_7$ group, can be obtained, for example, by an organometallic reaction of a propargyl halide and subsequent alkylation with a corresponding alkyl halide and optionally subsequent Lindlar hydrogenation.

An alternative structure of the lower chain starts from the aldehyde of formula XIV, which resulted from the Wittig-Horner reaction of aldehyde VI and subsequent reduction and oxidation.

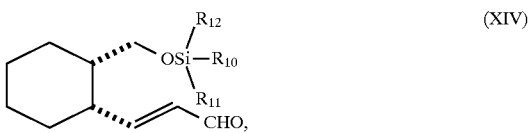
(XIV)

Wittig-Horner olefination of aldehyde XIII with a phosphonate of formula XV

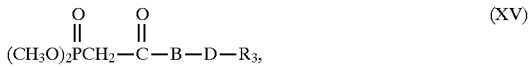
(CH$_3$O)$_2$PCH$_2$—C—B—D—R$_3$, (XV)

and reduction of the ketone that is produced then resulted in an alcohol of formula XII and, after acylation and silyl ether cleavage, in an alcohol of formula III, which optionally can be separated into diastereomers.

The compounds of general formula XIII are described in DE-A 42 27 790.6 or can be produced according to the process that is presented in DE-A 42 27 790.6.

After tosylation of the alcohol of general formula XIII and reaction with cyanide in dimethyl sulfoxide, the nitrile of formula XVI is obtained, which optionally can be protected by saponification of acid radical (OR$_2$) and subsequent silylation of the free hydroxy group.

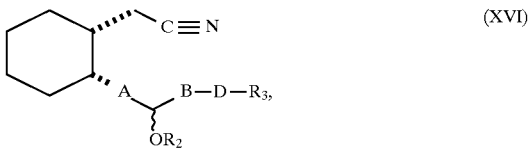
(XVI)

By reduction of the nitrile group in the compound of formula XVI, for example, with diisobutyl aluminum hydride and sodium borohydride, the alcohol of general formula II is then obtained.

The incorporation of the chemically and metabolically labile cis-$\Delta^{6,7}$ double bond of LTB$_4$ into a cis-1,2-substituted cyclohexyl ring results in a stabilization, whereby especially by further derivatization of the functional groups and/or structural changes of the lower side chain, $LTB_4$ derivatives that can act as $LTB_4$ antagonists were obtained (DE-A 39 17 597 and DE-A 42 27 790.6).

It has now been found that by substitution of the methylene group in 3-position (numbering system beginning with a carboxy-C atom with 1) and omission of the hydroxy group in 5-position in such leukotriene-$B_4$ derivatives, a prolonged duration of action, greater selectivity and better effectiveness can be achieved.

The compounds of formula I act in an antiinflammatory, antiallergic and antiproliferative manner. In addition, they have antimycotic properties. Consequently, the new leukotriene-$B_4$ derivatives of formula I represent valuable pharmaceutical active ingredients. The compounds of formula I are especially suitable for topical administration, since they exhibit a dissociation between desired topical effectiveness and undesirable systemic side effects.

The new leukotriene-$B_4$ derivatives of formula I are suitable in combination with the additives and vehicles that are commonly used in galenic pharmaceutics for topical treatment of diseases of the skin, in which leukotrienes play an important role, e.g.: contact dermatitis, eczemas of the most varied types, neurodermatoses, erythrodermia, pruritus vulvae et ani, rosacea, cutaneus lupus erythematosus, psoriasis, lichen ruber planus et verrucosis and similar skin diseases.

In addition, the new leukotriene-$B_4$ antagonists are suitable for the treatment of multiple sclerosis and symptoms of shock.

The production of the pharmaceutical agent specialties is carried out in the usual way by the active ingredients being converted with suitable additives to the desired form of administration, such as, for example: solutions, ointments, creams or patches.

In the thus formulated pharmaceutical agents, the active ingredient concentration depends on the form of administration. In lotions and ointments, an active ingredient concentration of 0.0001% to 3% is preferably used.

Further, the new compounds optionally in combination with the usual vehicles and adjuvants are also well-suited for the production of inhalants, which can be used to treat allergic diseases of the respiratory system, such as, for example, bronchial asthma or rhinitis.

Further, the new leukotriene-$B_4$ derivatives are also suitable in the form of capsules, tablets or coated tablets, which preferably contain 0.1 to 100 mg of active ingredient or are administered orally or in the form of suspensions, which preferably contain 1–200 mg of active ingredient per dosage unit, and are also administered rectally to treat diseases of the internal organs, in which leukotrienes play an important role, such as, e.g.: allergic diseases of the intestinal tract, such as colitis ulcerosa and colitis granulomatosa.

In these new forms of administration, the new $LTB_4$ derivatives, in addition to the treatment of diseases of internal organs with inflammatory processes, are also suitable for the treatment of diseases in which, leukotriene-dependent, the increased growth and the new formation of cells are important. Examples are leukemia (increased growth of white blood cells) or arteriosclerosis (increased growth of unstriped muscle cells of blood vessels).

The new leukotriene-$B_4$ derivatives can also be used in combination, such as, e.g., with lipoxygenase inhibitors, cyclooxygenase inhibitors, glucocorticoids, prostacyclin agonists, thromboxane antagonists, leukotriene-$D_4$ antagonists, leukotriene-$E_4$ antagonists, leukotriene-$F_4$ antagonists, phosphodiesterase inhibitors, calcium antagonists, PAF antagonists or other known forms of treatment of the respective diseases.

The following embodiments are used for a more detailed explanation of the process according to the invention. In the examples, diastereomers in 12-position that are not characterized in more detail were characterized as polar or nonpolar (e.g., diastereomer unpol (12)).

EXAMPLE 1

3-Oxa-5-[cis-(2R)-2-((1,3E)-(5R)-5-hydroxy-5-cyclohexyl-1,3-pentadienyl)-(1R)-cyclohexyl]-pentanoic acid-tert-butyl ester diastereomer pol (12)

1000 mg of bromoacetic acid-tert-butyl ester, 15.3 mg of tetrabutylammonium hydrogen sulfate and 3.1 ml of a 25% aqueous sodium hydroxide solution are added to a solution of 420 mg of (5R)-5-tert-butyl-dimethylsilyloxy-1-[cis-(1R)-1-(2-hydroxyethyl)-(2R)-cyclohex-2-yl]-5-cyclohexyl-(1E,3E)-pentadiene (diastereomer pol (12)) in 7.1 ml of toluene and stirred for 24 hours at room temperature under argon. Then, it is diluted with diethyl ether and washed neutral with water. It is dried on sodium sulfate, concentrated by evaporation in a vacuum, and the residue is purified by column chromatography on silica gel. With hexane/ether (9+1), 490 mg of tert-butyl ester is obtained as colorless oil.

IR(CHCl$_3$): 2912, 2850, 1740, 1378, 990, 835 cm$^{-1}$.

For silyl ether cleavage, 897 mg of tetrabutylammonium fluoride is added to a solution of 490 mg of the silyl ether, produced above, in 23 ml of tetrahydrofuran, and it is stirred for 4 hours at 24° C. under argon. 1.4 g of tetrabutylammonium fluoride is added again, and it is stirred for 20 hours at 24° C. Then, it is diluted with 200 ml of diethyl ether, washed three times with brine, dried on magnesium sulfate and concentrated by evaporation in a vacuum. The residue is purified by column chromatography on silica gel. With hexane/ethyl acetate (9+1), 310 mg of the title compound is obtained as colorless oil.

IR: 3610, 2930, 2858, 1745, 1450, 990, 945 cm$^{-1}$.

The starting material for the title compound above is produced as follows:

1a)

(5R)-5-Tert-butyl-dimethylsilyloxy-1-[cis-(1R)-1-(2-hydroxyethyl)-(2R)-cyclohex-2-yl]-5-cyclohexyl-(1E,3E)-pentadiene diastereomer pol (12)

4.4 g of p-toluenesulfonic acid chloride is added to a solution of 3.7 g of (5R)-5-acetoxy-1-[cis-(1S)-hydroxy methyl-(2S)-cyclohex-2-yl]-5-cyclohexyl-(1E,3E)-pentadiene (diastereomer pol (12)) (this compound is described in DE-A 42 27 790.6 or can be produced according to DE-A 42 27 790.6; diastereomer pol (12) means that after the chromatographic diastereomeric separation, the 12β(here 12R)-configuration was categorized as the polar allylic alcohol in 12-position (leukotriene-$B_4$ numbering system)) in 19.6 ml of pyridine at 0° C., and it is stirred for 24 hours at 24° C. Then, two pieces of ice are added to it, stirred for 2 hours and diluted with 400 ml of diehtyl ether. It is shaken in succession with 20 ml of water, twice with 20 ml of 10% aqueous sulfuric acid each, once with 20 ml of water, once with 20 ml of 5% aqueous sodium bicarbonate solution and three times with 20 ml of water each. It is dried with sodium sulfate and concentrated by evaporation in a vacuum. In this case, 5.4 g of tosylate is obtained, which is further used without additional purification.

To introduce nitrile, 5.4 g of the tosylate, produced above, in 46 ml of dimethyl sulfoxide is dissolved, 1.2 g of sodium cyanide is added and stirred for 24 hours at 85° C. under argon. Then, it is cooled, poured onto 50 ml of ice water, extracted three times with 200 ml of ethyl acetate each, the organic phase is washed neutral with water, dried with sodium sulfate and concentrated by evaporation in a vacuum. The residue is purified by column chromatography on silica gel. In this case, 3.24 g of nitrile is obtained as colorless oil.

IR: 2923, 2850, 2245, 1735, 1240, 995, 975 cm$^{-1}$.

For acetate cleavage, 1.3 g of anhydrous sodium carbonate is added to a solution of 1.5 g of nitrile, produced above, in 66 ml of methanol, and it is stirred for 4 hours at 24° C. under argon. Then, it is acidified with 10% aqueous sulfuric acid to pH 6, concentrated by evaporation in a vacuum and the residue is taken up in diethyl ether. It is washed neutral with brine, dried on sodium sulfate and concentrated by evaporation in a vacuum. In this case, 1.5 g of alcohol is obtained, which is further used without-additional purification.

For silyl ether formation, 1 g of imidazole and 1.14 g of tert-butyldimethylsilyl chloride are added to a solution of 1.5 g of the alcohol, produced above, in 12.6 ml of dimethylformamide and stirred for 24 hours at 24° C. It is diluted with diethyl ether, shaken with 20 ml of a 10% aqueous sulfuric acid, with 20 ml of water, with 20 ml of a saturated aqueous sodium bicarbonate solution and washed neutral with water. It is dried on sodium sulfate and concentrated by evaporation in a vacuum. The residue is purified by column chromatography on silica gel. In this case, 1.83 g of silyl ether is obtained as colorless oil.

IR: 2930, 2858, 2250, 993, 838 cm$^{-1}$.

For reduction of the nitrile group, 15 ml of an approximately 1.2 molar solution of diisobutylaluminum hydride in toluene is added in drops at –70° C. to a solution of 1.83 g of the silyl ether, produced above, in 48 ml of toluene, and it is stirred for 30 minutes at –70° C. Then, 1.5 ml of isopropanol and then 7.5 ml of water are added in drops, stirred for 2 hours at 22° C., filtered, washed with toluene and concentrated by evaporation in a vacuum. The thus obtained aldehyde is dissolved in 45 ml of methanol, mixed at –20° C. with 1.05 g of sodium borohydride and stirred for 50 minutes at –20° C. Then, it is diluted with diethyl ether, washed neutral with water, dried on sodium sulfate and concentrated by evaporation in a vacuum. The residue is purified by column chromatography on silica gel. In this case, 800 mg of the title compound is obtained as colorless oil.

IR: 3350, 2923, 2853, 990, 835 cm$^{-1}$.

EXAMPLE 2
3-Oxa-5-[cis-(2R)-2-((1E,3E)-(5R)-5-hydroxy-5-cyclohexyl-1,3-pentadienyl)-(1R)-cyclohexyl]-pentanoic acid diastereomer pol (12)

7.6 ml of a 0.5N sodium hydroxide solution is added to a solution of 310 mg of tert-butyl ester, produced according to Example 1, in 7.6 ml of methanol at 24° C., and it is stirred for 24 hours at 24° C. Then, it is acidified with 10% aqueous sulfuric acid to pH 5–6 and diluted with ethyl acetate. The organic phase is washed neutral with brine, dried on magnesium sulfate and concentrated by evaporation in a vacuum. The residue is purified by column chromatography on silica gel. In this case, 229 mg of the title compound is obtained as colorless oil.

IR: 3450, 2929, 2857, 1738, 1450, 1138, 990, 950 cm$^{-1}$.

EXAMPLE 3
3-Oxa-5-[cis-(2R)-2-((1E,3E)-(5S)-5-hydroxy-5-cyclohexyl-1,3-pentadienyl)-(1R)-cyclohexyl]-pentanoic acid-tert-butyl ester diastereomer unpol (12)

Analogously to the process that is described in Example 1, 220 mg of the title compound is obtained as colorless oil from 335 mg of (5S)-5-tert-butyl-dimethylsilyloxy-1-[cis-(1R)-1-(2-hydroxyethyl)-(2R)-cyclohex-2-yl]-5-cyclohexyl-(1E,3E)-pentadiene (diastereomer unpol 12).

IR: 3660, 2928, 2858, 1745, 1450, 991, 946 cm$^{-1}$.

The starting material for the title compound above is produced as follows:

(5S)-5-Tert-butyl-dimethylsilyloxy-1-[cis-(1R)-1-(2-hydroxyethyl)-(2R)-cyclohex-2-yl]-5-cyclohexyl-(1E,3E)-pentadiene diastereomer unpol (12)

Analogously to Example 1a, 718 mg of the title compound is obtained as colorless oil from 3.3 g of (5S)-5-acetoxy-1-[cis-(1S)-1-hydroxymethyl-(2S)-cyclohex-2-yl]-5-cyclohexyl-(1E,3E)-pentadiene (diastereomer unpol (12) (this compound is described in DE-A 42 27 790.6 or can be produced according to DE-A 42 27 790.6. Diastereomer unpol (12) means that after the chromatographic diastereomeric separation, the 12α (here 12-S)-configuration was categorized as the nonpolar allylic alcohol in 12-position (leukotriene-B$_4$ numbering system)).

IR: 3445, 2945, 2855, 990, 835 cm$^{-1}$.

EXAMPLE 4
3-Oxa-5-[cis-(2R)-((1E,3E)-(5S)-5-hydroxy-5-cyclohexyl-1,3-pentadienyl)-(1R)-cyclohexyl]-pentanoic acid diastereomer unpol (12)

Analogously to Example 2, 125 mg of the title compound is obtained as colorless oil from 210 mg of tert-butyl ester that is produced according to Example 3.

IR: 3450, 2930, 2858, 1738, 1450, 992, 950 cm$^{-1}$.

EXAMPLE 5
3-Oxa-5-[cis-(2R)-2-((1E,3E)-(5S)-5-hydroxy-6,6-trimethylene-9-phenyl-1,3-nonadien-8[inyl)-(1R)-cyclohexyl]-pentanoic acid-tert-butyl ester diastereomer pol (12)

7.9 g of bromoacetic acid-tert-butyl ester, 121 mg of tetrabutylammonium hydrogen sulfate and 25 ml of a 25% aqueous sodium hydroxide solution are added to a solution of 4 g of (5S)-5-tert-butyldimethylsilyloxy-1-[cis-(1R)-1-(2-hydroxyethyl)-(2R)-cyclohex-2-yl]-6,6-trimethylene-9-phenyl-(1E,3E)-1,3-nonadien-8-ine (diastereomer pol (12)) in 50 ml of toluene, and it is stirred for 24 hours at room temperature under argon. Then, it is diluted with diethyl ether and washed neutral with water. It is dried on magnesium sulfate, concentrated by evaporation in a vacuum, and the residue is purified by column chromatography on silica gel. With hexane/ether (9+1), 3.9 g of tert-butyl ester is obtained as colorless oil.

IR: 2925, 2850, 1740, 1378, 990, 835 cm$^{-1}$.

For silyl ether cleavage, 16.1 g of tetrabutylammonium fluoride is added to a solution of 3.9 g of silyl ether, produced above, in 200 ml of tetrahydrofuran, and it is stirred for 4 hours at 24° C. Then, it is diluted with diethyl ether and washed three times with brine. It is dried on sodium sulfate and concentrated by evaporation in a vacuum. The residue is purified by column chromatography on silica gel. With hexane/ethyl acetate (8+2), 2.7 g of the title compound is obtained as a solid substance (melting point 53° C.).

IR: 3610, 2930, 2860, 1745, 1600, 1370, 990 cm$^{-1}$.

The starting material for the title compound above is produced as follows:

5a)
(5S)-5-Tert-butyldimethylsilyloxy-1-[cis-(1R)-1-(2-hydroxyethyl)-(2R)-cyclohex-2-yl]-6,6-trimethylene-9-phenyl-(1E,3E)-1,3-nonadien-8-ine diastereomer pol (12)

Analogously to Example 1a, 4 g of the title compound is obtained as colorless oil from 4.98 g of (5S)-5-acetoxy- 1-[cis-(1S)-1-hydroxymethyl)-(2S)-cyclohex-2-yl]-6l,6-trimethylene-9-phenyl-(1E,3E)-1,3-nonadien-8-ine (diastereomer pol (12)) (this compound is described in DE-A 42 27 790.6 or can be produced according to DE-A 42 27 790.6).

IR: 3620, 2922, 2850, 1600, 990, 835 cm$^{-1}$.

EXAMPLE 6

3-Oxa-5-[cis-(2R)-2-((1E,3E)-(5S)-5-hydroxy-6,6-trimethylene-9-phenyl-1,3-nonadien-8-inyl)-(1R)-cyclohexyl]-pentanoic acid diastereomer pol (12)

Analogously to Example 2, 1.36 g of the title compound is obtained as colorless oil from 1.68 g of the tert-butyl ester produced according to Example 5.

IR: 3610, 3520, 1730, 1600, 990 cm$^{-1}$.

EXAMPLE 7

3-Oxa-5-[cis-(2R)-2-((1E,3E)-(5S)-5-hydroxy-6,6-trimethylene-9-phenyl-1,3-nonadien-8-inyl)-(1R)-cyclohexyl]-pentanoic acid-tert-butyl ester diastereomer unpol (12)

Analogously to the process described in Example 1, 1.36 g of the title compound is obtained as colorless oil from 2.25 g of (5R)-5-tert-butyl-dimethylsilyloxy-1-[cis-(1R)-1-(2-hydroxyethyl)-(2R)-cyclohex-2-yl]-6,6-trimethylene-9-phenyl-(1E,3E)-1,3-nonadien-8-ine (diastereomer unpol (12)). IR: 3600, 2930, 2859, 1745, 1600, 990 cm$^{-1}$.

The starting material for the title compound above is produced as follows:

7a)
(5S)-5-Tert-butyl-dimethylsilyloxy-1-[cis-(1R)-1-(2-hydroxyethyl)-(2R)-cyclohex-2-yl]-6,6-trimethylene-9-phenyl-(1E,l3E)-1,3-nonadien-8-ine diastereomer unpol (12)

Analogously to Example 1a, 2.27 g of the title compound is obtained as oil from 3.48 g of (5R)-5-acetoxy-1-[cis-(1S)-1-hydroxymethyl-(2S)-cyclohex-2-yl]-6,6-trimethylene-9-phenyl-(1E,3E)-1,3-nonadien-8-ine (diastereomer unpol (12)) (this compound is described in DE-A 42 27 790.6).

IR: 3620, 2923, 2850, 1598, 990, 835 cm$^{-1}$.

EXAMPLE 8

3-Oxa-5-[cis-(2R)-2-((1E,3E)-(5R)-5-hydroxy-6,6-trimethylene-9-phenyl-1,3-nonadien-8-inyl)-(1R)-cyclohexyl]- pentanoic acid diastereomer unpol (12)

Analogously to Example 2, 790 mg of the title compound is obtained as colorless oil from 1 g of the tert-butyl ester that is produced according to Example 7.

IR: 3620, 3500, 2924, 2853, 1730, 1600, 990 cm$^{-1}$.

EXAMPLE 9

3-Oxa-5-[cis-(2R)-2-((1E,3E)-(5R,8S)-5-hydroxy-8,12-dimethyl-1,3,11-tridecatrienyl-(1R)-cyclohexyl]-pentanoic acid-tert-butyl ester diastereomer pol (12)

Analogously to the process described in Example 1, 280 mg of the title compound is obtained as colorless oil from 720 mg of (5R)-5-tert-butyl-dimethylsilyloxy-1-[cis-(1R)-1-(2-hydroxyethyl)-(2R)-cyclohex-2-yl]-8,12-dimethyl-(1E, 3E, 11E)-tridecatiene (diastereomer pol (12)).

IR (Film): 3500, 2929, 2860, 1742, 1599, 1369, 991 cm$^{-1}$.

The starting material for the title compound above is produced as follows:

9a)
(5R,8S)-5-Tert-butyl-dimethylsilyloxy]-1-[cis-((1R)-1-(2-hydroxyethyl)-(2R)-cyclohex-2-yl]-8,12-dimethyl-(1E,3E, 11E)-tridecatrienyl (diastereomer pol (12))

Analogously to Example 1a, 732 mg of the title compound is obtained as colorless oil from 1.95 g of (5R,8S)-5-acetoxy-1-[cis-(1S)-1-hydroxymethyl-(2S)-cyclohex-2-yl]-8,12-dimethyl-(1E,3E,11E)-tridecatrienyl (diastereomer pol (12)) (this compound is described in DE-A 42 27 790.6 or can be produced according to DE-A 42 27 790.6).

IR: 3440, 2948, 2856, 990, 835 cm$^{-1}$.

EXAMPLE 10

3-Oxa-5-[cis-(2R)-2-((1E,3E)-(5R,8S)-5-hydroxy-8,12-dimethyl-1,3,11-tridecatrienyl-(1R)-cyclohexyl]-pentanoic acid diastereomer pol (12)

Analogously to Example 2, 0.28 g of the title compound is obtained as colorless oil from 0.55 g of the tert-butyl ester produced according to Example 9.

IR: 3450, 2923, 2855, 1733, 990 cm$^{-1}$.

EXAMPLE 11

3-Oxa-5-[cis-(2R)-2-((1E,3E)-(5RS,7RS)-5-hydroxy-7-methyl-1,3-tridecadien-9-inyl)-(1R)-cyclohexyl]-pentanoic acid-tert-butyl ester diastereomer unpol (12)

Analogously to the process described in Example 1, 970 mg of the title compound is obtained as colorless oil from 1.26 g of (5RS)-5-tert-butyl-dimethylsilyloxy-1-[cis-(1R)-1-(2-hydroxyethyl)-(2R)-cyclohex-2-yl]-7-methyl-1,3-tridecadien-9-ine (diastereomer unpolar A).

IR: 3450, 2923, 2860, 1748, 1368, 1135, 990, 943 cm$^{-1}$.

The starting material for the title compound above is produced as follows:

11a)
(5RS,7RS)-5-Tert-butyl-dimethylsilyloxy-1-[cis-(1R)-1-(2-hydroxyethyl)-(2R)-cyclohex-2-yl]-7-methyl-1,3-tridecadien-9-ine diastereomer unpol A Analogously to Example 1a, 1.26 g of the title compound is obtained as colorless oil from 2.28 g of (5RS,7RS)-5-acetoxy-1-[cis-(1S)-1-hydroxymethyl-(2S)-cyclohex-2-yl]-7-methyl-1,3-tridecadien-9-ine (diastereomer unpol A) (this compound is described in DE-A 42 27 790.6 or can be produced according to DE-A 42 27 790.6).

IR: 3540, 2930, 2860, 990, 838, 777 cm$^{-1}$.

EXAMPLE 12

3-Oxa-5-[cis-(2R)-2-((1E,3E)-(5RS,7RS)-5-hydroxy-7-methyl-1,3-tridecadien-9-inyl)-(1R)-cyclohexyl]-pentanoic acid diastereomer unpol A Analogously to Example 2, 643 mg of the title compound is obtained as colorless oil from 770 mg of tert-butyl ester that is produced according to Example 11.

IR: 3440, 2930, 2860, 1735, 1135, 990 cm$^-$.

EXAMPLE 13

3-Oxa-5-[cis-(2R)-2-((1E,3E)-(5R,6RS)-5-hydroxy-6-methyl-9-phenyl-1,3-nonadien-8-inyl)-(1R)-cyclohexyl]-pentanoic acid-tert-butyl ester diastereomer pol (12)

Analogously to Example 1, 1.1 g of the title compound is obtained as colorless oil from 2.9 g of (5R,6RS)-5-acetoxy-1-[cis-(1S)-1-hydroxymethyl)-(2S)-cyclohex-2-yl]-6-methyl-9-phenyl-(1E,3E)-1,3-nonadien-8-ine (diastereomer pol (12)) (this compound is described in DE-A 42 27 790.6 or can be produced according to DE-A 42 27 790.6.

IR: 3600, 2930, 2858, 1746, 1600, 1371, 990 cm$^{-1}$.

EXAMPLE 14

3-Oxa-5-[cis-(2R)-2-((1E,3E)-(5R,6RS)-5-hydroxy-6-methyl-9-phenyl-1,3-nonadien-8-inyl)-(1R)-cyclohexyl]-pentanoic acid diastereomer pol (12)

Analogously to Example 2, 0.45 g of the title compound is obtained as colorless oil from 0.6 g of the tert-butyl ester that is produced according to Example 13.

IR: 3600, 3510, 1731, 1600, 990 cm$^{-1}$.

EXAMPLE 15

3-Oxa-5-[cis-(2R)-2-((1E,3E)-(5R)-5-hydroxy-5-cyclohexyl-1,3-pentadienyl)-(1R)-cyclohexyl]-pentanoic acid-methyl ester diastereomer pol (12)

An ethereal diazomethane solution is added in drops at 0° C. to a solution of 360 mg of the acid, produced according to Example 2, in 10 ml of diethyl ether until permanent yellow coloring, and it is stirred for 10 minutes at 0° C. Then, it is concentrated by evaporation in a vacuum, and the residue is purified by column chromatography on silica gel. With hexane/ethyl acetate (4+1), 360 mg of the title compound is obtained as colorless oil.

IR: 3450, 2922, 2850, 1755, 1450, 1260, 1140, 990 cm$^{-1}$.

EXAMPLE 16

3-Oxa-5-[cis-(2R)-2-((1E,3E)-(5S)-5-hydroxy-6,6-trimethylene-9-phenyl-1,3-nonadien-8-inyl)-(1R)-cyclohexyl]-pentanoic acid methyl ester diastereomer pol (12)

Analogously to Example 15, 94 mg of the title compound is obtained as colorless oil from 100 mg of the carboxylic acid that is produced according to Example 6.

IR: 3500, 2922, 2850, 2215, 1755, 1598, 1210, 991 cm$^{-1}$.

EXAMPLE 17

3-Oxa-5-[cis-(2R)-2-((1E,3E)-(5S)-5-hydroxy-6,6-trimethylene-9-phenyl-1,3-nonadien-8-inyl)-(1R)-cyclohexyl]-pentanoic acid phenacyl ester diastereomer pol (12)

63 mg of phenacyl bromide and 1 ml of a solution of triethylamine in acetone (production: 350 mg of triethylamine is dissolved in 10 ml of acetone) are added to a solution of 118 mg of the carboxylic acid, produced according to Example 6, in 2 ml of acetone. It is stirred for 4 hours at 24° C. and then diluted with 50 ml of diethyl ether. It is shaken twice with water, dried on magnesium sulfate and concentrated by evaporation in a vacuum. The residue is purified by chromatography on silica gel. With hexane/ethyl acetate (3+2), 144 mg of the title compound is obtained as colorless oil. IR: 3510, 2923, 2852, 2220, 1767, 1705, 1598, 990, 967 cm$^{-1}$.

EXAMPLE 18

3-Oxa-5-[cis-(2R)-2-((1E,3E)-(5R)-5-hydroxy-5-cyclohexyl-1,3-pentadienyl)-(1R)-cyclohexyl]-pentanoic acid-(2,3-dihydroxy-propyl)-amide diastereomer pol (12)

450 mg of 3-amino-propane-1,2-diol is added to a solution of 150 mg of the methyl ester, produced according to Example 6, in 3 ml of acetonitrile, and it is stirred for 24 hours at 80° C. Then, it is concentrated by evaporation in a vacuum, and the residue is purified by column chromatography on silica gel. With dichloromethane/methanol (9+1), 165 mg of the title compound is obtained as colorless oil.

IR: 3400, 2922, 2852, 1660, 1543, 990 cm$^{-1}$.

EXAMPLE 19

3-Oxa-5-[cis-(2R)-2-((1E,3E)-(5R)-5-hydroxy-5-cyclohexyl-1,3-pentadienyl)-(1R)-cyclohexyl]-pentanoic acid-[tris-(hydroxymethyl)-methyl]-amide diastereomer pol (12)

390 mg of tris(hydroxymethyl)methylaminomethane is added to a solution of 180 mg of the methyl ester, produced according to Example 6, in 0.1 ml of dimethyl sulfoxide, and it is stirred for 24 hours at 24° C. Then, the reaction mixture is purified by column chromatography on silica gel. With dichloromethane/methanol (9+1), 217 mg of the title compound is obtained as colorless oil.

IR: 3350, 2922, 2850, 1655, 1530, 990 cm$^{-1}$.

EXAMPLE 20

3-Oxa-5-[cis-(2R)-2-((1E,3E)-(5R)-5-hydroxy-5-cyclohexyl-1,3-pentadienyl)-(1R)-cyclohexyl]-pentanoic acid-butylamide diastereomer pol (12)

100 mg of the tert-butyl ester that is produced according to Example 1 is refluxed for 48 hours under argon in 2 ml of butylamine. Then, it is concentrated by evaporation in a vacuum, and the residue is purified by column chromatography. With hexane/ethyl acetate (1+1), 63 mg of the title compound is obtained as colorless oil.

IR: 3600, 3420, 2925, 2858, 1665, 1533, 1448, 990 cm$^{-1}$.

EXAMPLE 21

Tris-(hydroxymethyl)-aminomethane salt of 3-oxa-5-[cis-(2R)-2-((1E,3E)-(5R)-5-hydroxy-5-cyclohexyl-1,3-pentadienyl)-(1R)-cyclohexyl]-pentanoic acid diastereomer pol (12)

0.054 ml of an aqueous tris(hydroxymethyl) aminomethane solution (production: 8.225 g of tris (hydroxymethyl)aminomethane in 15 ml of water) is added to a solution of 100 mg of the carboxylic acid, produced according to Example 2, in 17.3 ml of acetonitrile at 80° C., stirred for 1 hour at 80° C., 1 hour at 55° C., 48 hours at 45° C. and 48 hours at 24° C. The formed crystals are sectioned off, washed with some acetonitrile, and the crystals are dried at 24° C. in a vacuum. In this case, 134 mg of the title compound is obtained as colorless crystals (melting point: 113°–114° C.)

IR: 3350, 2922, 2850, 1590 (broad), 1450, 992 cm$^{-1}$.

EXAMPLE 22

Tris-(hydroxymethyl)-aminomethane salt of 3-oxa-5-[cis-(2R)-2-((1E,3E)-(5R)-5-hydroxy-6,6-trimethylene-9-phenyl-1,3-nonadien-8-inyl-(1R)-cyclohexyl]-pentanoic acid diastereomer pol (12)

Analogously to Example 21, 149 mg of the title compound is obtained as colorless crystals (melting point 114°–116° C.) from 124 mg of the carboxylic acid that is produced according to example 6.

IR(KBr): 3350, 2922, 2850, 1588 (broad), 992 cm$^{-1}$.

We claim:

1. A leukotriene-B$_4$ of formula I,

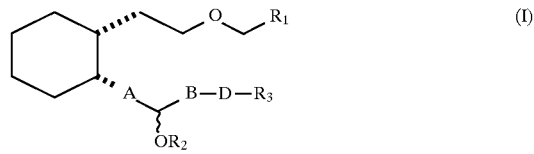

in which

R$_1$ represents CH$_2$OH, CH$_3$, CF$_3$, COOR$_4$, or CONR$_5$R$_6$,

R$_2$ represents H or an aryl or sulfonyl group of a carboxylic or sulfonic acid with 1–15 C atoms, R$_3$ symbolizes H; C$_1$–C$_{14}$ alkyl or C$_2$–C$_{14}$ alkenyl, each optionally substituted with halogen or phenyl optionally substituted as described below for C$_6$–C$_{10}$ aryl; C$_3$–C$_{10}$ cycloalkyl, optionally substituted with alkyl or halogen; C$_6$–C$_{10}$ aryl, optionally substituted with halogen, phenyl, C$_1$–C$_4$ alkyl, C$_1$–C$_4$ alkoxy, fluoromethyl, chloromethyl, trifluoromethyl, carboxyl or hydroxy; or a 5- to 6-membered aromatic heterocyclic ring with at least 1 heteroatom, R$_4$ means hydrogen; C$_1$–C$_{10}$ alkyl, optionally substituted with halogen, alkoxy, C$_{6-10}$-aryl, C$_{6-10}$-aroyl, di-C$_{1-4}$-alkylamino or tri-C$_{1-4}$-alkylamino, the aryl and aryl groups being optionally substituted as described above for C$_{6-10}$ aryl for R$_3$; C$_3$–C$_{10}$ cycloalkyl optionally substituted with $C_{1-4}$ alkyl; $C_6-C_{10}$ aryl optionally substituted by halogen, phenyl, $C_1-C_4$ alkyl, $C_1-C_4$ alkoxy, fluoromethyl, chloromethyl, trifluoromethyl, carboxyl or hydroxy; $CH_2$—CO—($C_6-C_{10}$) aryl, wherein the $C_6-C_{10}$-aryl group is optionally substituted as described above under $R_3$; or a 5- to 6-membered ring with at least 1 heteroatom, A symbolizes a trans, trans—CH=CH—CH=CH, a —$CH_2CH_2$—CH=CH— or a tetramethylene group, B symbolizes a $C_1-C_{10}$ straight-chain or branched-chain alkylene group, which optionally can be substituted by fluorine or the group $$-\underset{(CH_2)_n}{\overset{}{C}}-CH_2- \quad \text{or} \quad -CH_2-\underset{(CH_2)_n}{\overset{}{C}}-$$

D means a direct bond, oxygen, sulfur, —C≡C—, —CH=$CR_7$, or together with B can also mean a direct bond, $R_5$ and $R_6$ are the same or different, and represent H or $C_1-C_4$ alkyl or $R_6$ represents H and $R_5$ represents a $C_1-C_{15}$ aryl or sulfoyl group of a carboxylic or sulfonic acid, and are optionally substituted with OH, $R_7$ means H, $C_1-C_5$ alkyl, chlorine, or bromine, n is 2–5, and, if $R_4$ means hydrogen, a salt thereof with a physiologically compatible base, or a cyclodextrin clathrate therof.

2. A pharmaceutical composition comprising an effective amount of leukotriene-$B_4$ according to claim 1 and a pharmaceutically acceptable carrier.

3. A process for the production of a leukotriene-$B_4$ derivative according to claim 1, wherein an alcohol of formula II $$\text{(II)}$$

in which A, B, D, $R_2$ and $R_3$ have the above-indicated meaning, optionally under protection of free hydroxy groups in $R_2$, is reacted with an alkyl halide or haloacetic acid compound of formula III, $$X-CH_2-R_1 \quad \text{(III)},$$

whereby X represents chlorine, bromine or iodine, and $R_1$ represents —$CH_3$, $CF_3$ or —$CH_2OR_9$, in which $R_9$ means a readily cleavable either radical, is etherified in the presence of a base and then, optionally, in any sequence isomers are separated, protected hydroxy groups are released and/or a free hydroxy group is esterified and/or the 1-hydroxy group is oxidized to carboxylic acid and/or double bonds are hydrogenated and/or an esterified carboxyl group is saponified and/or reduced and/or a carboxyl group is esterified and/or a free carboxyl group is converted to an amide or a carboxyl group is converted to a salt with a physiologically compatible base.

4. A method of treating an inflammatory disease comprising administering an effective amount of a leukotriene-$B_4$ of claim 1 to a patient suffering from said disease.

5. The method of claim 4, wherein the disease is an inflammatory disease in which leukocytes invade the affected tissue, a skin disease in which leukotrienes play a role, or a disease of internal organs in which leukotrienes play a role.

6. A leukotriene-$B_4$ of claim 1, wherein $R_1$ is $CH_2OH$, $CONR_5R_6$, or $COOR_4$, and $R_4$ is a hydrogen atom, $C_1-C_{10}$ alkyl, $C_2-C_{10}$ alkenyl, $C_5-C_6$ cycloalkyl, phenyl optionally substituted with chlorine, bromine, phenyl, $C_{1-4}$ alkyl, $C_2-C_4$ alkenyl, $C_{1-4}$ alkoxy, $C_2-C_4$ alkenoxy chloromethyl, fluoromethyl, trifluoromethyl, carboxy or hydroxy.

7. A leukotriene-$B_4$ of claim 1, wherein A is trans—CH=CH—CH=CH or tetramethylene.

8. A leukotriene-$B_4$ of claim 1, wherein B is $C_1-C_{10}$ alkylene, $C_{2-10}$ alkenylene, each of which optionally can be substituted with fluorine, or with $$-\underset{(CH_2)_n}{\overset{}{C}}-CH_2-$$

wherein n=2–5.

9. A leukotriene-$B_4$ of claim 1, wherein D is a direct bond, oxygen, sulfur, —C≡C— or —CH=$CR_7$ with $R_7$ being hydrogen, $C_{1-5}$ alkyl, chlorine or bromine.

10. A leukotriene-$B_4$ of claim 1, wherein $R_3$ is a hydrogen atom, $C_{1-10}$ alkenyl, $C_2-C_{10}$ alkenyl, $C_5-C_6$ cycloalkyl, or phenyl optionally substituted with chlorine, bromine, phenyl, $C_{1-4}$ alkyl, $C_2-C_4$ alkenyl, $C_{1-4}$ alkoxy, $C_2-C_4$ alkenoxy, chlorometyl, fluoromethyl, trifluoromethyl, carboxy or hydroxy.

11. A leukotriene-$B_4$ of claim 1, wherein $R_1$ is $CH_2OH$, $CONR_5R_6$, or $COOR_4$ wherein $R_4$ is a hydrogen atom, $C_1-C_4$ alkyl, or $C_2-C_4$ alkenyl.

12. A leukotriene-$B_4$ of claim 1, wherein $R_2$ is hydrogen or an aryl or sulfonyl group of a carboxylic or sulfonic acid with 1–6 C atoms.

13. A leukotriene-$B_4$ of claim 1, wherein $R_3$ is a hydrogen atom, $C_{1-10}$, alkyl, or $C_2-C_{10}$ alkenyl.

14. A leukotriene-$B_4$ of claim 1, wherein A is a trans, trans—CH=CH—CH=CH or tetramethylene.

15. A leukotriene-$B_4$ of claim 1, wherein B is a $C_1-C_5$ alkylene.

16. A leukotriene-$B_4$ of claim 1, wherein D is a direct bond or a —C≡C or a —CH=$CR_7$ wherein $R_7$ is hydrogen, $C_{1-5}$ alkyl, or $C_2-C_5$ alkenyl.

17. A leukotriene-$B_4$ of claim 1, wherein $R_3$ is an aryl substituted in the 3- and 4-position of the phenyl ring by fluorine, chlorine, alkoxy or trifluoromethyl, or in the 4-position of the phenyl ring by hydroxy.

18. A leukotriene-$B_4$ of claim 1, wherein $R_3$ is 2-furyl, 2-thienyl, 2-pyridyl, 3-pyridyl, 4-pyridyl, oxazolyl, thiazolyl, pyrimidinyl, pyridazinyl, pyrazinyl, 3-furyl or 3-thienyl.

19. A leukotriene-$B_4$ of claim 1, wherein $R_4$ is a aryl subsituted in the 3- and 4-position of the phenyl ring by fluorine, chlorine, alkoxy or trifluoromethyl, or in the 4-position of the phenyl ring by hydroxy.

20. A leukotriene-$B_4$ of claim 1, wherein $R_4$ is 2-furyl, 2-thienyl, 2-pyridyl, 3-pyridyl, 4-pyridyl, oxazolyl, thiazolyl, pyrimidinyl, pyridazinyl, 3-furyl, 3-thienyl or 2-tetrazolyl.

21. A leukotriene-$B_4$ of claim 1, wherein $R_5$ and $R_6$ are methyl.

* * * * *